US008858442B2

(12) United States Patent
Osumi

(10) Patent No.: US 8,858,442 B2
(45) Date of Patent: Oct. 14, 2014

(54) ULTRASONIC DIAGNOSTIC APPARATUS AND ULTRASONIC IMAGE PROCESSING APPARATUS

(75) Inventor: Ryota Osumi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 787 days.

(21) Appl. No.: 12/540,584

(22) Filed: Aug. 13, 2009

(65) Prior Publication Data

US 2010/0041993 A1 Feb. 18, 2010

(30) Foreign Application Priority Data

Aug. 14, 2008 (JP) ................. 2008-208952

(51) Int. Cl.
*A61B 8/00* (2006.01)
*G06T 5/30* (2006.01)
*A61B 8/08* (2006.01)
*G06T 5/00* (2006.01)
*G06T 5/10* (2006.01)

(52) U.S. Cl.
CPC ......... *A61B 8/08* (2013.01); *G06T 2207/20016* (2013.01); *G06T 5/30* (2013.01); *G06T 2207/10132* (2013.01); *G06T 5/002* (2013.01); *A61B 8/0858* (2013.01); *G06T 2207/30004* (2013.01); *G06T 2207/20036* (2013.01); *G06T 2207/20064* (2013.01); *G06T 5/10* (2013.01)
USPC ........... 600/443; 382/128; 382/226; 382/276; 382/278; 702/189; 702/193

(58) Field of Classification Search
USPC .......... 600/407, 437, 441, 443, 544; 382/128, 382/169, 170, 171, 172, 256, 257, 258, 266, 382/295, 296, 297, 298
See application file for complete search history.

(56) References Cited

U.S. PATENT DOCUMENTS

| 2004/0066960 A1* | 4/2004 | McLaren et al. ............. 382/128 |
| 2005/0100208 A1* | 5/2005 | Suzuki et al. ................ 382/157 |
| 2006/0078182 A1* | 4/2006 | Zwirn et al. ................. 382/128 |
| 2006/0127880 A1* | 6/2006 | Harris et al. ..................... 435/4 |
| 2007/0065009 A1* | 3/2007 | Ni et al. ....................... 382/173 |
| 2007/0071354 A1* | 3/2007 | Florent et al. ................ 382/266 |
| 2009/0088638 A1 | 4/2009 | Sato et al. |

FOREIGN PATENT DOCUMENTS

| JP | 9-330415 | 12/1997 |
| JP | 2000-224421 | 8/2000 |

(Continued)

OTHER PUBLICATIONS

"Morphological Reconstruction", The Mathworks, Inc., http://www.mathworks.com/access/helpdesk/help/toolbox/images/f18-16264.html, 11 pages.

(Continued)

*Primary Examiner* — Unsu Jung
*Assistant Examiner* — Michael N Fisher
(74) *Attorney, Agent, or Firm* — Oblon, Spivak, McClelland, Maier & Neustadt, L.L.P.

(57) ABSTRACT

A speckle pattern is removed from each image such that each image obtained by a multi-resolution decomposition is decomposed into a low-band signal component, a high-band signal horizontal component, a high-band signal vertical component, and a high-band signal diagonal component, the decomposed signal components are subjected to a morphological reconstruction process, and then a multi-resolution reconstruction is performed.

18 Claims, 12 Drawing Sheets

(56) References Cited

FOREIGN PATENT DOCUMENTS

| | | |
|---|---|---|
| JP | 2000-279416 | 10/2000 |
| JP | 2001-22929 | 1/2001 |
| JP | 2001-034751 | 2/2001 |
| JP | 2001-118058 | 4/2001 |
| JP | 2005-334677 | 12/2005 |
| JP | 2006-91790 | 4/2006 |
| JP | 2006-325629 | 12/2006 |
| JP | 2007-256338 | 10/2007 |

OTHER PUBLICATIONS

Office Action issued May 8, 2012, in Japanese Patent Application No. 2008-208952 with English translation.

Office Action issued Apr. 1, 2014 in Japanese Patent Application No. 2013-048325 (with English Translation).

\* cited by examiner

ULTRASONIC DIAGNOSTIC APPARATUS AND ULTRASONIC IMAGE PROCESSING APPARATUS

CROSS-REFERENCE TO RELATED APPLICATIONS

This application is based upon and claims the benefit of priority from prior Japanese Patent Application No. 2008-208952, filed Aug. 14, 2008, the entire contents of which are incorporated herein by reference.

BACKGROUND OF THE INVENTION

1. Field of the Invention

The present invention relates to image processing apparatus, and more particularly, to an ultrasonic diagnostic apparatus which transmits an ultrasonic wave into a patient and obtains diagnostic information inside the patient on the basis of the ultrasonic wave reflected from the inside of the patient, and an ultrasonic image processing apparatus which uses an ultrasonic image obtained by the ultrasonic diagnostic apparatus.

2. Description of the Related Art

In the ultrasonic diagnostic inspection, a heartbeat or a fetus's movement state may be obtained in real time just by touching a body surface with an ultrasonic probe and the ultrasonic diagnostic inspection may be repeated due to the reliability of the ultrasonic diagnostic inspection. In addition, since the system size of the ultrasonic diagnostic apparatus is smaller than those of other diagnostic apparatuses such as an X-ray diagnostic apparatus, a CT diagnostic apparatus, and an MRI diagnostic apparatus, the ultrasonic diagnostic inspection may be easily performed by disposing the ultrasonic diagnostic apparatus on the side of the bed. For this reason, the ultrasonic diagnostic inspection is a simple diagnostic method. Although the size of the ultrasonic diagnostic apparatus used in the ultrasonic diagnostic inspection is different depending on the types of the functions thereof, a small-sized ultrasonic diagnostic apparatus which can be carried by one hand is developed. Unlike the X-ray diagnostic apparatus, the ultrasonic diagnostic inspection is not influenced by an exposure, and may be used in the obstetrics and gynecology or home medical treatment. In such an ultrasonic diagnostic apparatus, generally, a two-dimensional tomographic image is obtained by scanning a specific section of the patient using an ultrasonic probe having ultrasonic vibrators arranged in one dimension. However, in recent years, three-dimensional biological information (volume data) can be collected by spatially scanning the inside of the patient using a two-dimensional array ultrasonic probe having ultrasonic vibrators arranged in two dimensions.

However, the received signals obtained from the plural adjacent patient tissues interfere with each other due to the phase information thereof, and an image pattern obtained by a viewing method different from the case of synthesizing only the amplitude information, that is, a speckle pattern is created. Since the speckle pattern often disturbs an operation of accurately observing the shape and position of the boundary of the patient tissue, various treatment methods of removing the speckle pattern are proposed.

As one method, there is known a method in which a target image is subjected to a multi-resolution decomposition by means of a Wavelet transform and a Wavelet inverse transform, and the respective decomposed images are subjected to a predetermined process. The multi-resolution decomposition and the multi-resolution reconstruction are used to reduce the noise of the image or to synthesize plural images without appearing unnatural. For example, as disclosed in JP-A-2000-224421, for the purpose of removing a noise, the Wavelet multi-resolution decomposition through several levels is performed, an opening and closing process based on a mathematical morphology is performed on a low-band component of the decomposed image, and then a difference therebetween is obtained to extract a noise component. Then, a noise removing process is performed on the basis of the result, and the obtained image is provided to the next level decomposition.

As another method, as disclosed in JP-A-2007-256338, for the purpose of improving a resolution by removing a discontinuous feeling at a boundary between an overlapped region and a non-overlapped region upon synthesizing plural sheets of images having an overlapped region obtained by a compound scanning method in the ultrasonic diagnostic apparatus, plural sheets of images to be synthesized are subjected to the multi-resolution decomposition, and the decomposed images are subjected to a filter calculation process such as an average and a maximum value of the plural sheets of images.

In addition, the compound scanning method is one of the speckle pattern removing methods, but in the speckle pattern removing method not based on the scanning method, a filter process may be performed on the high-band component of the image having been subjected to the multi-resolution decomposition.

Meanwhile, for the purpose of extracting a shape or reducing a noise, a method called a morphological reconstruction is known as disclosed in H. Arefi, M. Hahn "A Morphological reconstruction algorithm for separating off-terrain points from terrain points laser scanning data", ISPRS WG III/3, III/4, V/3 Workshop "Laser scanning 2005", Enschede, the Netherlands, Sep. 12-14, 2005 or "Morphological Reconstruction", MathWorks, Inc. http://www.mathworks.com/access/helpdesk_r13/help/toolbox/images/morph10.html.

However, the known speckle pattern removing method has problems as below.

That is, according to a simple process such as a threshold value setting and a weighted value or the morphological opening and closing process used in JP-A-2000-224421, it is possible to reduce the speckle pattern. However, the resultant image gives an artificial feeling to an observer.

Further, according to the morphological reconstruction process, it is possible to obtain an image in which a regional maximum value is reduced and a bright portion of the speckle pattern is cut. However, a dark portion of the speckle pattern is not removed only by the morphological reconstruction process, and hole shapes are formed at several positions on the image. In addition, since the speckle pattern reduced portion is not smooth, the boundary and the uneven portion are visibly noticed.

BRIEF SUMMARY OF THE INVENTION

The present invention is contrived in consideration of the above-described circumstances, and an object of the invention is to provide an ultrasonic diagnostic apparatus capable of creating an ultrasonic image having an appropriately removed speckle pattern and not artificial but smooth image quality, and an ultrasonic image processing apparatus.

According to an aspect of the present invention, there is provided an ultrasonic diagnostic apparatus including: a multi-resolution decomposition unit which performs a multi-resolution decomposition on ultrasonic image data so as to obtain first image data corresponding to a low-band signal component and at least one of second image data corresponding to a high-band signal component; a reduction process unit which performs a regional maximum value reduction process of reducing a regional maximum value lower than a first level and a regional minimum value reduction process of reducing a regional minimum value higher than a second level on the first image data and the at least one of the second image data; and a reconstruction unit which performs a multi-resolution reconstruction by using the first image data and the at least one of the second image data having been subjected to the regional maximum value reduction process and the regional minimum value reduction process so as to create a reconstruction image.

According to another aspect of the present invention, there is provided an ultrasonic image processing apparatus including: a multi-resolution decomposition unit which performs a multi-resolution decomposition on ultrasonic image data so as to obtain first image data corresponding to a low-band signal component and at least one of second image data corresponding to a high-band signal component; a reduction process unit which performs a regional maximum value reduction process of reducing a regional maximum value lower than a first level and a regional minimum value reduction process of reducing a regional minimum value higher than a second level on the first image data and the at least one of the second image data; and a reconstruction unit which performs a multi-resolution reconstruction by using the first image data and the at least one of the second image data having been subjected to the regional maximum value reduction process and the regional minimum value reduction process so as to create a reconstruction image.

DETAILED DESCRIPTION OF THE INVENTION

Figure 1:
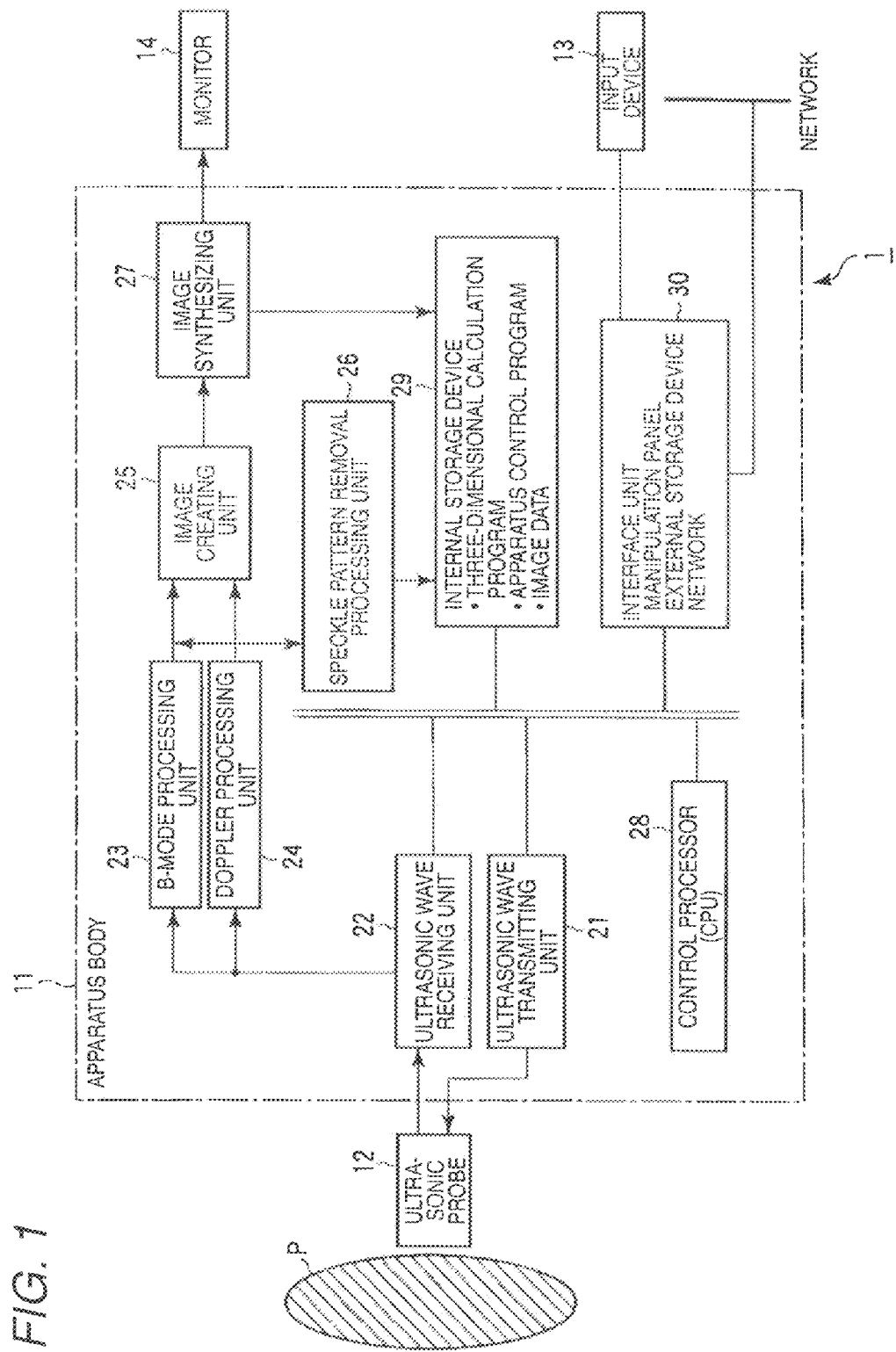
FIG. 1 is a block diagram showing a configuration of an ultrasonic diagnostic apparatus according to a first embodiment.

Hereinafter, the first and second embodiments of the invention will be described with reference to the accompanying drawings. Additionally, in the below description, the same reference numerals will be given to the components having the substantially same functions and configurations, and the repetitive description thereof will be made if necessary.

First Embodiment

FIG. 1 is a block diagram showing a configuration of an ultrasonic diagnostic apparatus 1 according to the first embodiment. As shown in FIG. 1, an ultrasonic diagnostic apparatus 1 includes an ultrasonic probe 12, an input device 13, a monitor 14, an ultrasonic wave transmitting unit 21, an ultrasonic wave receiving unit 22, a B-mode processing unit 23, a Doppler processing unit 24, an image creating unit 25, a speckle pattern removal processing unit 26, an image synthesizing unit 27, a control processor (CPU) 28, an internal storage device 29, and an interface unit 30. Hereinafter, the functions of the respective constituents of the ultrasonic diagnostic apparatus 1 will be described.

The ultrasonic probe 12 generates ultrasonic waves on the basis of a driving signal output from the ultrasonic wave transmitting unit 21, and includes plural piezoelectric vibrators which convert waves reflected from a patient into electric signals, a matching layer which is provided in the piezoelectric vibrators, a backing material which prevents the ultrasonic waves from being transmitted backwards from the piezoelectric vibrators, and the like. When the ultrasonic waves are transmitted from the ultrasonic probe 12 to a patient P, the transmitted ultrasonic waves are sequentially reflected by discontinuous surfaces of acoustic impedance of a body tissue, and are transmitted to the ultrasonic probe 12 in the form of echo signals. The amplitudes of the echo signals are dependent on the acoustic impedance difference of the discontinuous surfaces. In addition, in the case where the transmitted ultrasonic pulses are reflected by a surface of a moving blood stream, a moving cardiac wall, or the like, a frequency shift of the echo signal occurs depending on a velocity component of a moving object in an ultrasonic wave transmitting direction due to the Doppler Effect.

The input device 13 is connected to the apparatus body 11, and includes various switches, buttons, a track ball, a mouse, a keyboard, and the like which are used to allow an operator to input various instructions, conditions, ROI (region of interest) setting instructions, image quality condition setting instructions, and the like to the apparatus body 11. For example, when the operator operates an end button or a FREEZE button of the input device 13, the ultrasonic wave transmitting and receiving operation ends, and the ultrasonic diagnostic apparatus is maintained in a pause state.

The monitor 14 displays blood stream information (an average velocity image, a distribution image, a power image, and the like), morphological information (general B-mode image) inside the body, and the like thereon in a predetermined form on the basis of a video signal output from the image creating unit 25.

The ultrasonic wave transmitting unit 21 includes a trigger generating circuit, a delay circuit, a pulser circuit, and the like which are not shown in the drawing. The pulser circuit repeatedly generates rate pulses at a predetermined rate frequency fr Hz (period; 1/fr second) so as to form the transmitted ultrasonic waves. The delay circuit converges the ultrasonic waves for each channel into a beam and gives a delay time required for determining the transmitting directivity to each rate pulse. The trigger generating circuit applies a driving pulse to the probe 12 at a timing based on the rate pulse.

The ultrasonic wave receiving unit 22 includes an amp circuit, an A/D converter, an adder, and the like which are not shown in the drawing. The amp circuit amplifies the echo signal obtained via the probe 12 for each channel. The A/D converter gives a time required for determining the receiving directivity to the amplified echo signal, and the amplified echo signal is subjected to an adding process by the adder. By means of the adding process, a reflection component in the direction according to the receiving directivity of the echo signal is emphasized, and an ultrasonic wave transmitting and receiving synthetic beam is formed by the receiving directivity and the transmitting directivity.

The B-mode processing unit 23 receives the echo signal from the ultrasonic wave transmitting unit 21, and performs a log amplifying process, an envelope detecting process, and the like so as to create data in which the signal strength is represented by a luminance. The data is transmitted to the image creating unit 25, and is displayed as a B-mode image on the monitor 14, where in the B-mode image, the strength of the reflected wave is represented by a luminance.

The Doppler processing unit 24 analyzes the velocity component in the frequency on the basis of the echo signal transmitted from the ultrasonic wave transmitting unit 21 and extracts an echo component of a blood stream, a tissue, or a visualizing agent using the Doppler effect so as to obtain blood stream information such as an average velocity, a distribution, and a power at plural points.

The image creating unit 25 creates an ultrasonic image by using data transmitted from the B-mode processing unit 23, the Doppler processing unit 24, and the speckle pattern removal processing unit 26.

The speckle pattern removal processing unit 26 performs a process (speckle pattern removal process) according to a speckle removal function to be described later by using the B-mode image data obtained by the B-mode processing unit 23 or the Doppler-mode image data obtained by the Doppler processing unit 24. Further, in the embodiment, for the detailed description, the speckle pattern removal processing unit 26 performs the speckle pattern removal process by using the B-mode image data.

The image synthesizing unit 27 synthesizes the image obtained by the image creating unit 25 with texts and scales of various parameters, and outputs the resultant image as a video signal to the monitor 14.

The control processor 28 functions as an information processing device (calculator), and controls the operation of the apparatus body of the ultrasonic diagnostic apparatus. The control processor 28 reads out an exclusive program for realizing the speckle pattern removal function, which is described later, and a control program for performing a predetermined scan sequence from the internal storage device 29, and loads the programs in its memory so as to perform a calculation control or the like for various processes.

The internal storage device 29 stores a predetermined scan sequence for collecting plural volume data in accordance with a different viewing angle setting, an exclusive program for performing the speckle pattern removal function to be described later, a control program for performing the image creating and displaying process, a program for creating diagnostic information (a patient ID, a doctor's opinion, and the like), a diagnostic protocol, a transmitting-receiving condition, and a body mark, and other data groups. Further, if necessary, the internal storage device 29 is used to store the images obtained by the image creating unit 25, the volume data creating unit 26, and the image synthesizing unit 27. The data of the internal storage device 29 can be transmitted to an external peripheral device via the interface unit 30.

The interface unit 30 is an interface for the input device 13, a network, and a new external storage device (not shown). The data, the analysis result, or the like of the ultrasonic image or the like obtained by the devices can be transmitted to other devices via the network by the interface unit 30.

Speckle Pattern Removal Function

Next, the speckle pattern removal function of the ultrasonic diagnostic apparatus 1 will be described. This function is to remove the speckle pattern from the respective images in such a manner that respective images obtained by a multi-resolution decomposition are decomposed into a low-band signal component, a high-band signal component, and the like, and a morphological reconstruction process is performed on the decomposed signal components so as to perform a multi-resolution reconstruction.

Figure 2:
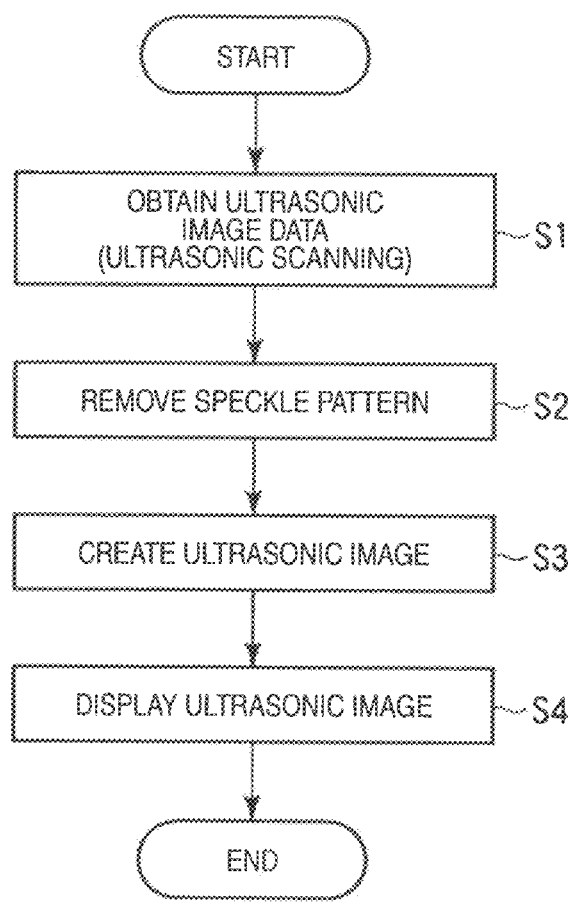
FIG. 2 is a flowchart showing a sequence of a process in which a speckle pattern removal function is realized by the ultrasonic diagnostic apparatus.

FIG. 2 is a flowchart showing a sequence of a process in which the speckle pattern removal function is realized by the ultrasonic diagnostic apparatus. By referring to FIG. 2, the contents of the speckle pattern removal process will be described. In addition, in the case where the speckle pattern removal function is realized by an ultrasonic image processing apparatus, the processes in Step S2 to Step S4 shown in FIG. 2 are performed by using the previously obtained image data.

Image Data Acquisition: Step S1

First, an ultrasonic scanning is performed on a predetermined portion of the patient, and the echo signal is obtained for each frame obtained from the predetermined portion. The B-mode processing unit 23 creates plural two-dimensional image data (raw data) by using the echo signal obtained for each frame (Step S1).

Speckle Pattern Removal Process: Step S2

The speckle pattern removal processing unit 26 performs the speckle pattern removal process on plural two-dimensional image data created by the B-mode processing unit 23 (Step S2).

Figure 3:
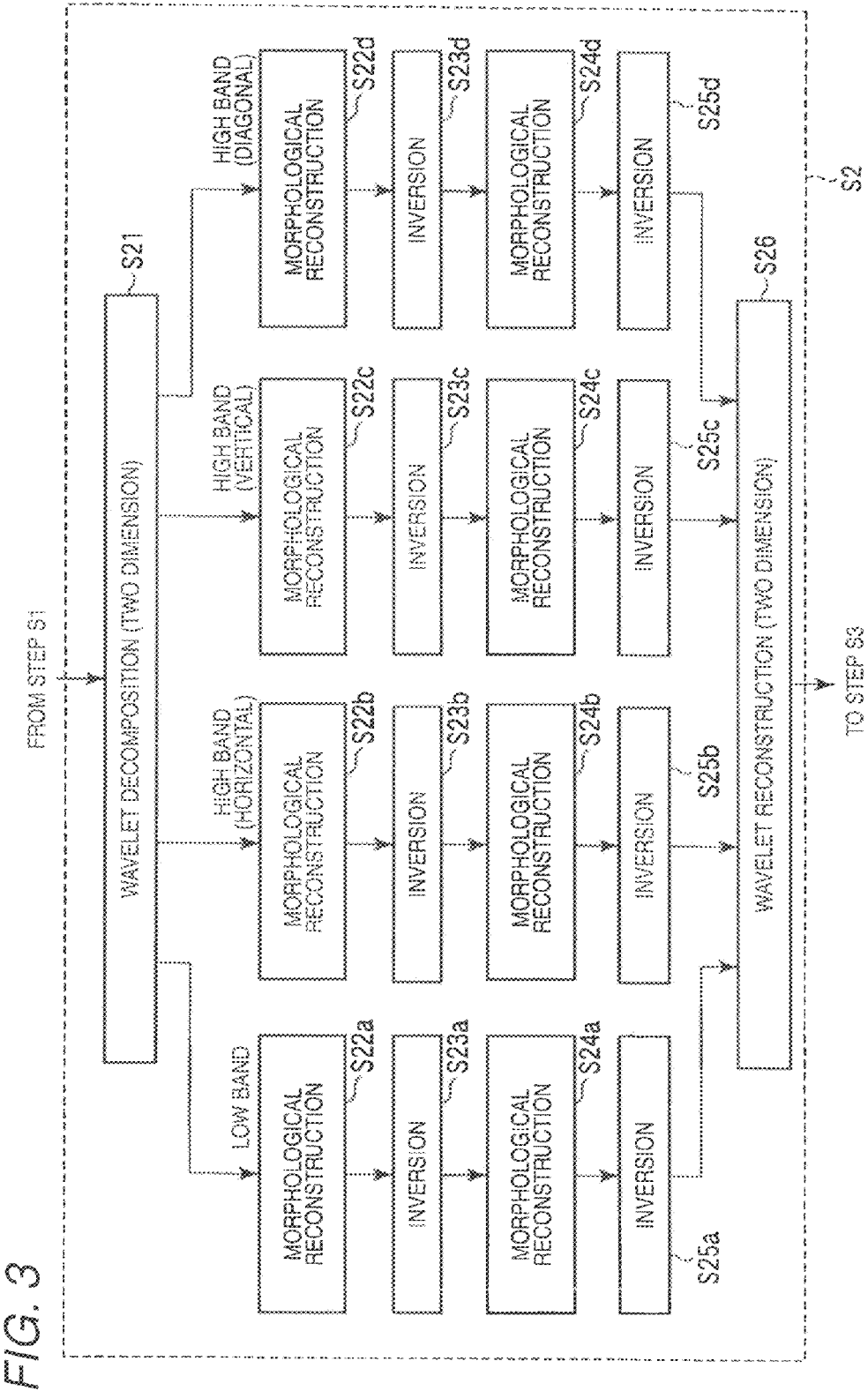
FIG. 3 is a flowchart showing a sequence of a speckle pattern removal process in Step S2.

FIG. 3 is a flowchart showing a sequence of the speckle pattern removal process in Step S2. As shown in FIG. 3, first, the speckle pattern removal processing unit 26 performs the multi-resolution decomposition on the respective images (Step S21). Here, for the detailed description, the multi-resolution decomposition using a Wavelet transform (discrete Wavelet transform) is performed so that the respective images are decomposed into a low-band signal component, a high-band signal horizontal component, a high-band signal vertical component, and a high-band signal diagonal component using the multi-resolution decomposition. However, the speckle pattern removal process is not limited to a multi-resolution decomposition method using the Wavelet transform, but other methods such as a Laplacian Pyramid method, a Fresnel transform, and a Gabor transform may be used.

As a result of the multi-resolution decomposition of the image, it is possible to obtain an A image (A: Approximation) corresponding to the low-band signal component, an H image (H: Horizontal detail) corresponding to the high-band signal horizontal component, a V image (V: Vertical detail) corresponding to the high-band signal vertical component, and a D image (D: Diagonal detail) corresponding to the high-band signal diagonal component.

Next, the speckle pattern removal processing unit 26 performs a morphological reconstruction process on the respective images corresponding to the respective signal components (i.e., the low-band signal component, the high-band signal horizontal component, the high-band signal vertical component, and the high-band signal diagonal component) so as to reduce a regional maximum value (Step S22a to Step S22d).

Figure 4:
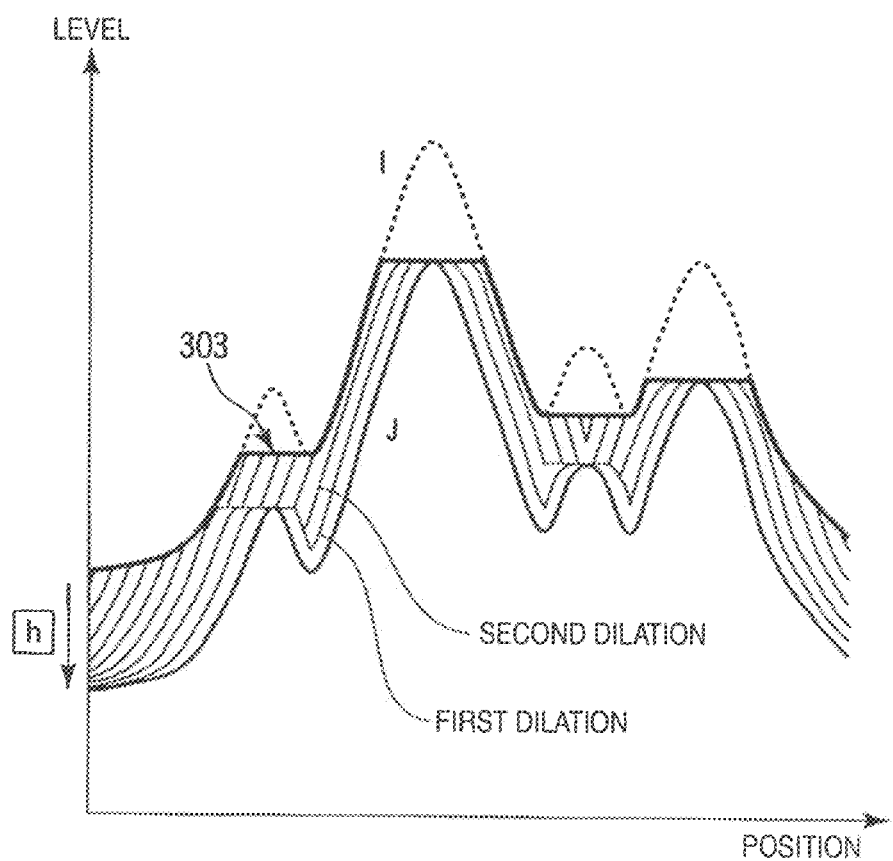
FIG. 4 is a diagram illustrating a concept of a morphological reconstruction process in Step S22.

FIG. 4 is a diagram illustrating a concept of the morphological reconstruction process in Step S22. Additionally, in FIG. 4, the description is made in one dimension for the easy description. The image obtained from the B-mode processing unit 23 is set to a mask "I". The image obtained by subtracting a level h from the mask is set to a marker "J". Between the input image (mask) I and the marker J, the following Equation (1) is obtained.

$$J=I-h \quad (1)$$

Here, a shape in the vicinity of a pixel is defined as a structuring element, and a morphological dilation process is performed on the marker using the structuring element. Here, the morphological dilation indicates a process in which the maximum value of the structuring element is obtained for each pixel of the input image and the maximum value is set to a pixel of an output image. When the structuring element is represented as "S", the morphological dilation calculation is expressed by the following Equation (2).

$$\delta(J)=J\oplus S \quad (2)$$

Here, "$\oplus$" is an operator showing the dilation.

However, the dilation of the marker is limited by the mask. That is, in the dilation, the minimum value of each pixel of the dilative marker and the mask is limited by the mask.

$$\delta_f(J)=(J\oplus S)\hat{\ }I \quad (3)$$

Here, "$\hat{\ }$" is an operator showing the minimum value for each pixel.

The calculation is repeated by applying a new marker to the left term of Equation (3). When the i-th marker is denoted by "$J_i$" and the i+1-th marker is denoted by $J_{i+1}$, the following Equation (4) is obtained between $J_i$ and $J_{i+1}$.

$$J_{i+1}=(J_i\oplus S)\hat{\ }I \quad (4)$$

Further, in FIG. 4, the state where the marker is sequentially dilated by the repeated calculation under the limitation of the mask is depicted by the thin line.

The speckle pattern removal processing unit 26 compares the $J_i$ with $J_{i+1}$ for each repetition in the repeated calculation loop. When the $J_{i+1}$ is equal to $J_i$, the speckle pattern removal processing unit 26 determines that the marker is converged, and ends the repeated calculation loop. The converged marker, that is, the reference numeral 303 shown in FIG. 4 is the reconstructed image. As understood from FIG. 4, the image convergence number is different depending on the slope of the mask. In the steep slope, the image is converged by repeating the calculation a small number of times. However, in the gentle slope, the image is converged by repeating the calculation a large number of times.

Further, since it takes time to calculate all pixels of the image whenever repeating the calculation, if the converged pixels are not subjected to the calculation of Equation (4), it is possible to rapidly perform the speckle pattern removal process. Also, since it is possible to obtain the speckle pattern removal advantage by repeating the calculation a predetermined number of times, the calculation may stop after repeating the calculation a predetermined number of times.

Next, the speckle pattern removal processing unit 26 inverts the respective signal components having been subjected to the morphological reconstruction process (Step S23a to Step S23d), and performs the morphological reconstruction process for reducing the regional minimum value (Step S24a to Step S24d).

The speckle pattern removal processing unit 26 reduces the region minimum value by performing any one of processes (a) and (b).

(a) Assuming that the input image is set to the mask and the image obtained by adding the level h to the mask is set to the marker, a morphological erosion process is performed on the marker. The erosion of the marker is limited by the mask, and the erosion is repeated until the marker is converged.

(b) The image is inverted, the morphological reconstruction process in Equation (4) is performed on the inverted image, and then the obtained image is inverted again.

The results of the (a) and (b) are equal when the level h is equal to the structuring element S, and the image having the reduced regional minimum value is obtained. For this reason, when the (a) and (b) are performed on the resultant of the morphological reconstruction process, it is possible to obtain the image in which both the bright portion and the dark portion of the speckle pattern are deleted. In addition, the process sequence of the (a) is very similar to the regional maximum value reduction process. The morphological dilation process is a process in which the maximum value of the structuring element is obtained from each pixel of the input image and the maximum value is set to the pixel of the output image.

When the input image (mask) is denoted by "I", the marker is denoted by "J=I+h", the structuring element is denoted by "S", and the operator showing the minimum value for each pixel is denoted by "v", the following Equation (5) corresponding to the regional maximum value reduction process in Equation (4) is obtained.

$$J_{i+1}=(J_i\ominus S)\vee I \quad (5)$$

Here, "$\ominus$" is an operator showing the erosion.

The speckle pattern removal processing unit 26 repeats the calculation until the J is not changed. In each image obtained in this way, the regional maximum value and the regional minimum value are independently deleted.

Next, the speckle pattern removal processing unit 26 inverts the respective signal components having been subjected to the morphological reconstruction process for reducing the regional minimum value (Step S25a to Step S25d), and performs a multi-resolution synthesis on the respective signal components so as to create the respective images in which the speckle pattern is removed (Step S26).

Ultrasonic Image Creation and Display: Step S3 and Step S4

The image creating unit 25 creates the ultrasonic image by using the image data having been subjected to the speckle pattern removal process (Step S3). The created ultrasonic image is synthesized with the texts, the scales, or the like of various parameters by the image synthesizing unit 27, and the synthesized image is displayed as a predetermined form on the monitor 14 (Step S4).

In addition, in the description with reference to FIGS. 2 and 3, the image having been subjected to the morphological reconstruction process for reducing the regional maximum value is inverted, and the inverted image is subjected to the morphological reconstruction process for reducing the regional minimum value. On the contrary, first, the image having been subjected to the morphological reconstruction process for reducing the regional minimum value may be inverted, and the inverted image may be subjected to the morphological reconstruction process for reducing the regional maximum value. In addition, even when the inversion process in Step S23a to Step S23d, the morphological reconstruction process (for reducing the regional minimum value) in Step S24a to Step S24d, and the inversion process in Step S25a to Step S25d are omitted as occasion demands, it is possible to obtain the sufficient speckle pattern removal advantage.

With the above-described configuration, it is possible to obtain the following advantage.

Figure 5:
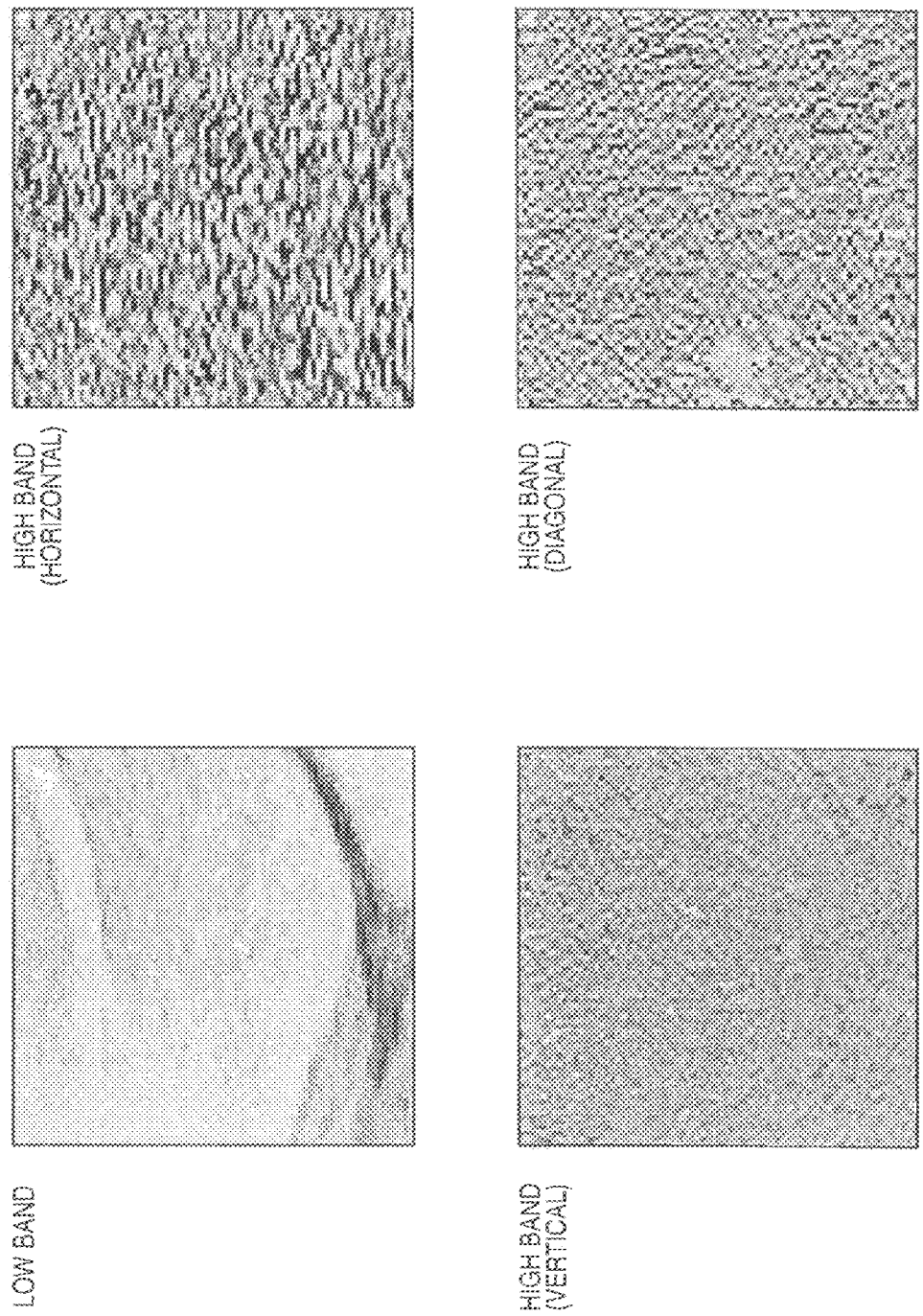
FIG. 5 is a diagram illustrating an advantage of the ultrasonic diagnostic apparatus according to the first embodiment.
Figure 6:
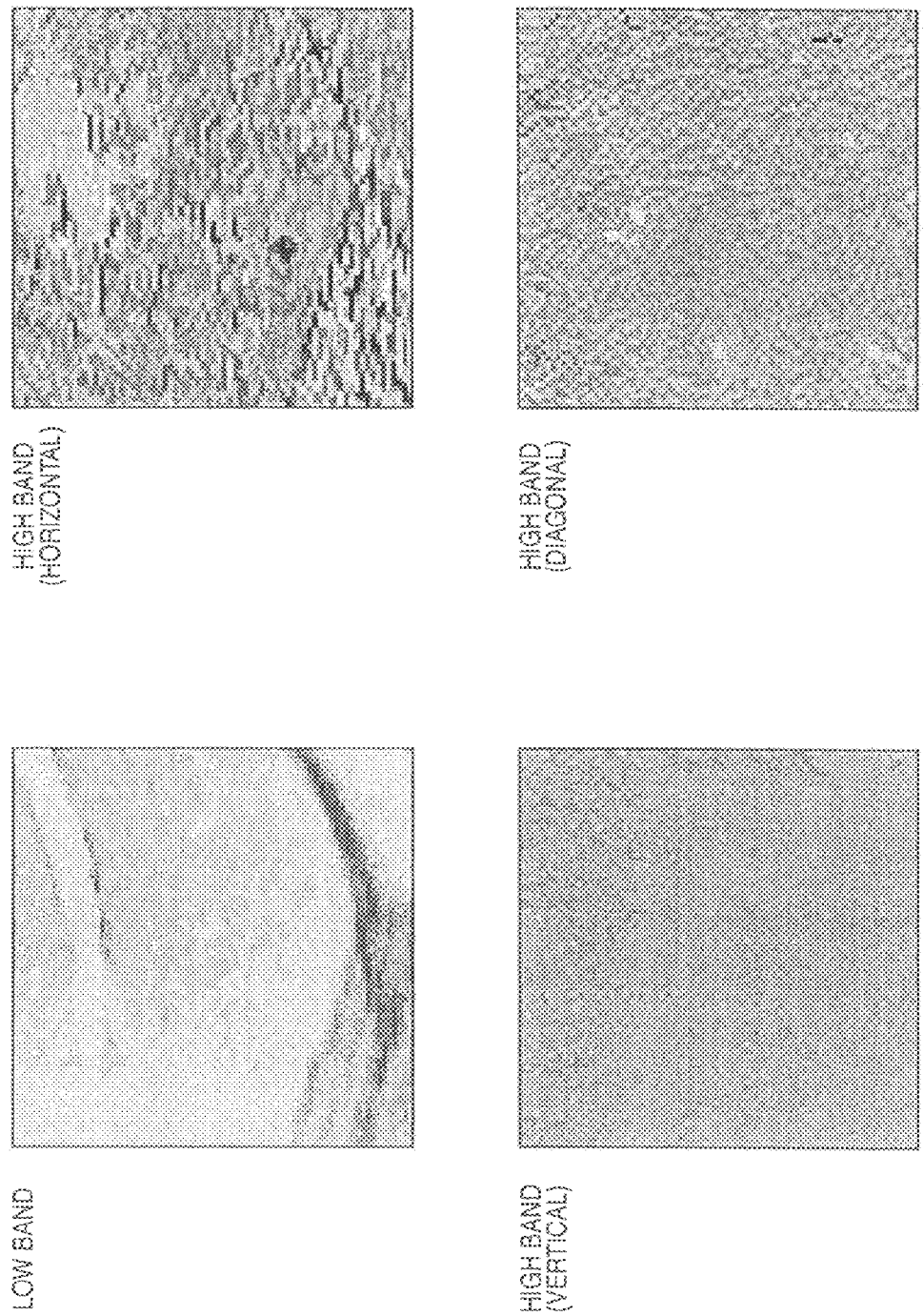
FIG. 6 is a diagram illustrating the advantage of the ultrasonic diagnostic apparatus according to the first embodiment.
Figure 7:
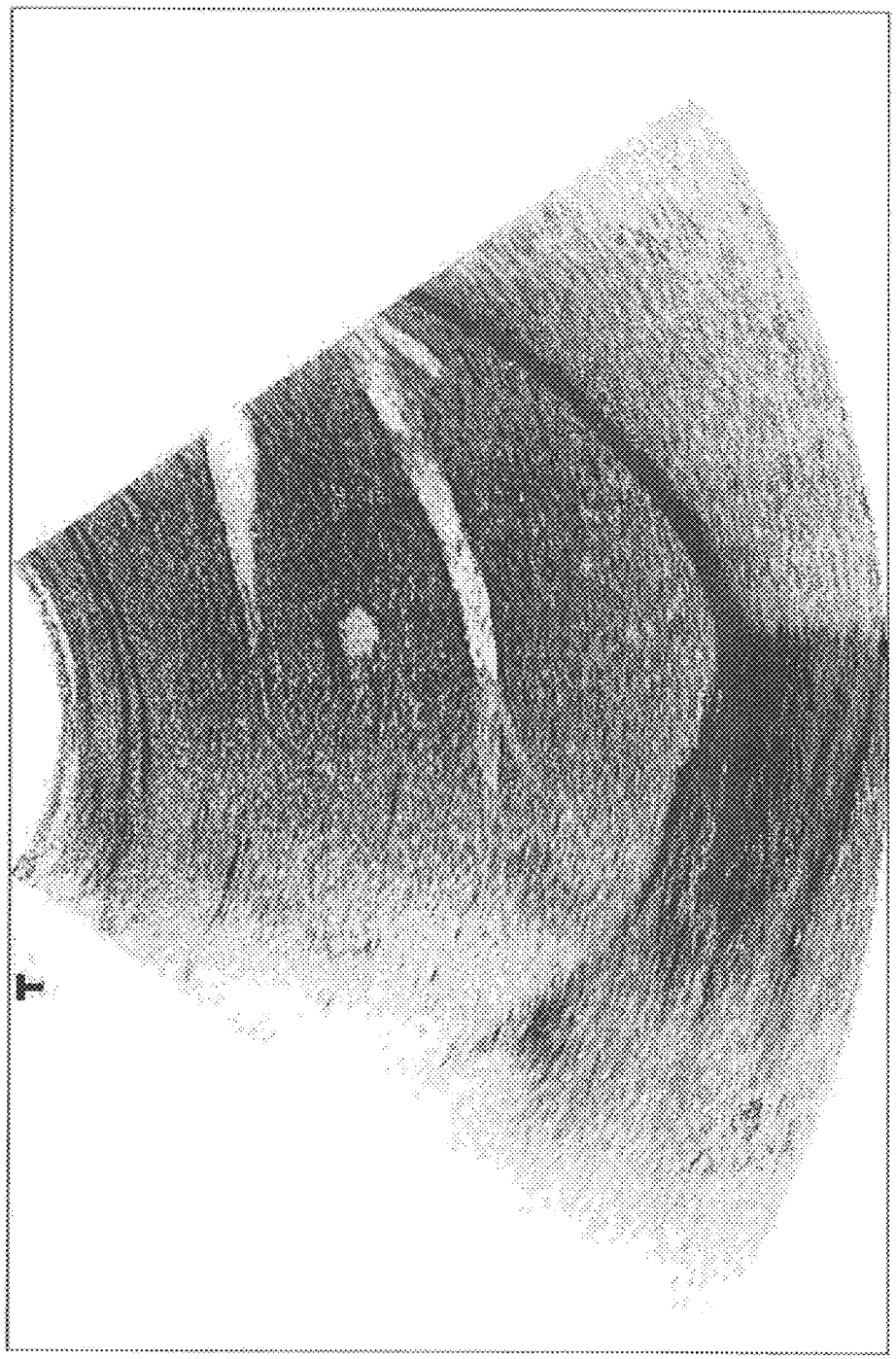
FIG. 7 is a diagram illustrating the advantage of the ultrasonic diagnostic apparatus according to the first embodiment.
Figure 8:
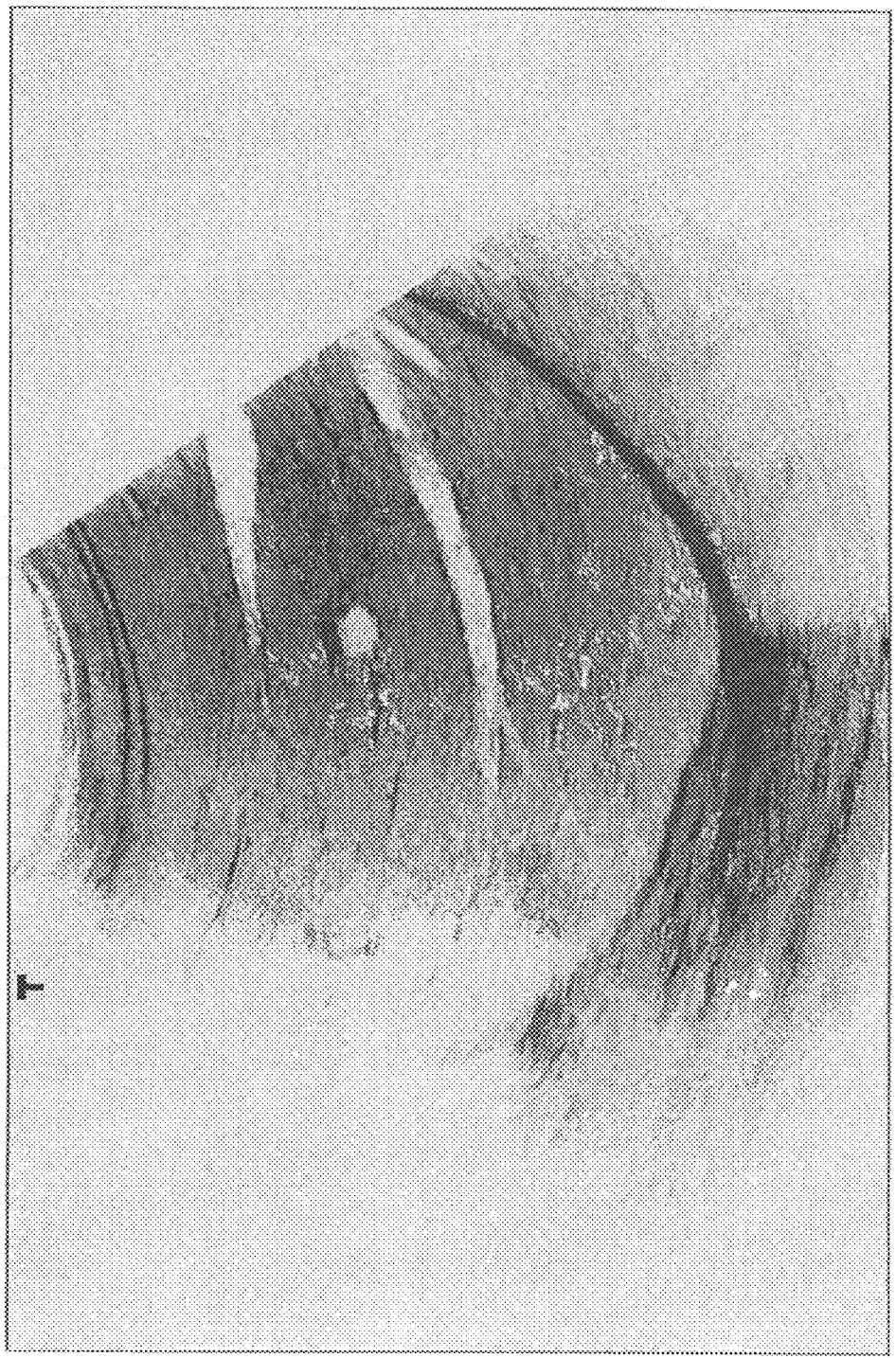
FIG. 8 is a diagram illustrating the advantage of the ultrasonic diagnostic apparatus according to the first embodiment.

According to the ultrasonic diagnostic apparatus, the respective images are subjected to the multi-resolution decomposition using the Wavelet decomposition so as to obtain the respective signal components. The level h and the structuring element S are set to the decomposed high-band signal component, the decomposed low-band signal component, and the like, and the morphological reconstruction process is performed thereon independently. Accordingly, it is possible to smoothen the respective signal components of the images as shown in FIG. 6 compared with the case where the morphological reconstruction process is not performed as shown in FIG. 5. Additionally, the respective images are reconstructed by using the respective signal components having been subjected to the morphological reconstruction process. Accordingly, it is possible to obtain the ultrasonic image in which the speckle pattern is smoothly and minutely removed as shown in FIG. 8 compared with the image which is not subjected to the speckle pattern removal process as shown in FIG. 7. Particularly, it is possible to appropriately remove the dark portion of the speckle pattern compared with the case where only the regional maximum value reduction process is used. Further, it is possible to prevent hole shapes from being formed at several positions on the image. Furthermore, it is possible to smoothly reduce the speckle pattern compared with the case where the regional maximum value reduction process and the regional minimum value reduction process are used. As a result, it is possible to remove the boundary portion and the uneven portion so as not to be visibly noticed.

Second Embodiment

Next, a second embodiment of the invention will be described. The ultrasonic diagnostic apparatus 1 according to the embodiment obtains the volume data by means of an oscillation scanning using a one-dimensional array probe or a volume scanning using a two-dimensional array probe, and performs the speckle pattern removal process on the volume data. In addition, the volume data corresponding to a target of the speckle pattern removal process may be any one of the B-mode volume data and the Doppler volume data. In the below description, for the detailed description, the case of using the B-mode volume data will be exemplified.

Figure 9:
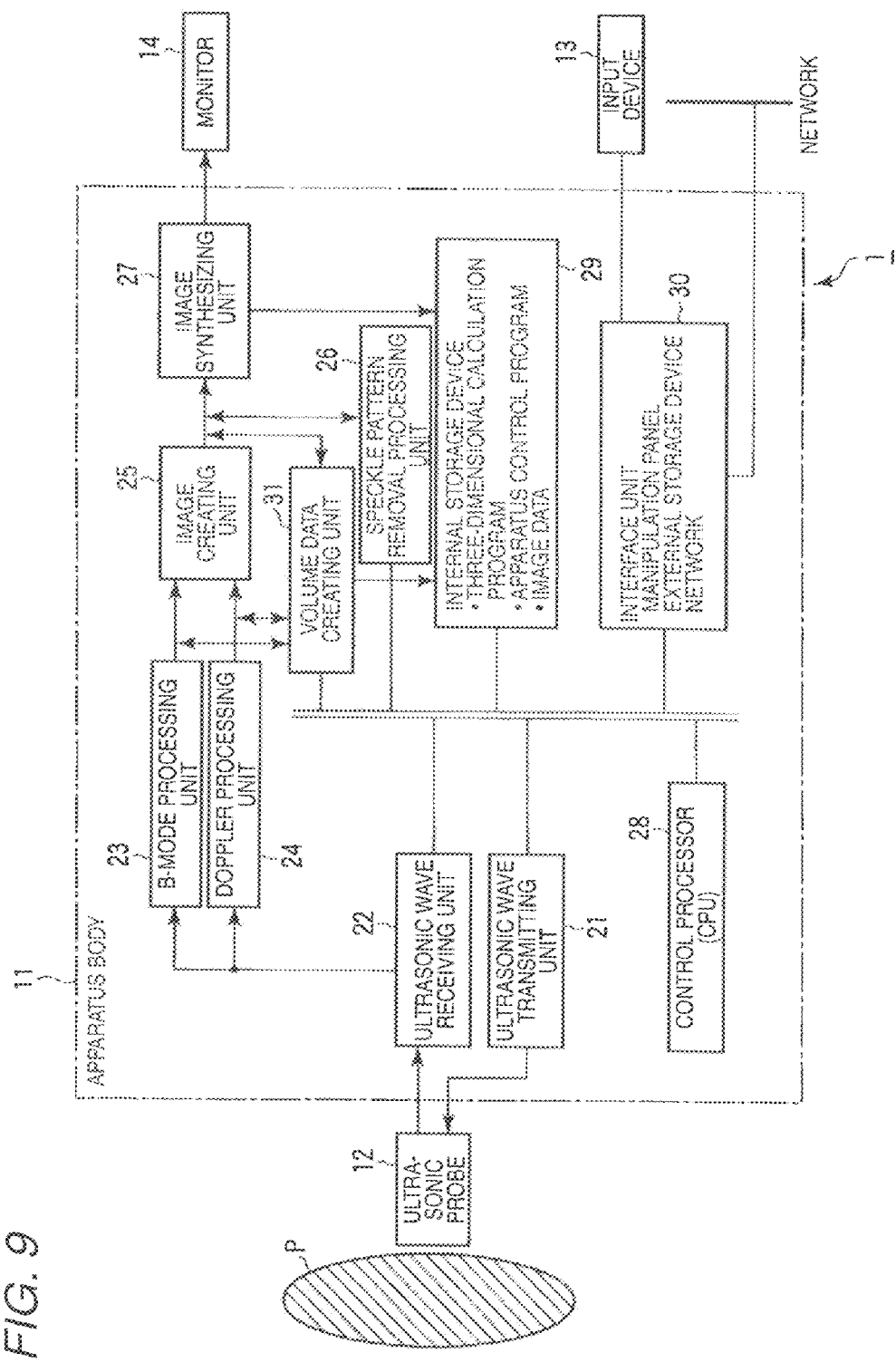
FIG. 9 is a block diagram showing a configuration of the ultrasonic diagnostic apparatus according to a second embodiment.

FIG. 9 is a block diagram showing a configuration of the ultrasonic diagnostic apparatus 1 according to the second embodiment. Only the configuration that is different from that of the ultrasonic diagnostic apparatus 1 according to the first embodiment shown in FIG. 1 will be described.

The ultrasonic probe 12 is capable of scanning the three-dimensional region of the patient by using the ultrasonic wave. For example, the ultrasonic probe 12 is the oscillation probe which mechanically oscillates plural vibrators arranged in one direction in a direction perpendicular to the arrangement direction or the two-dimensional array probe in which the ultrasonic vibrators are arranged in a two-dimensional matrix shape.

The volume data creating unit 31 creates the volume data for each time phase of the three-dimensional scanning region by using the image data obtained from the B-mode processing unit 23 and the Doppler processing unit 24.

The speckle pattern removal processing unit 26 performs the speckle pattern removal process to be described later on the created volume data.

Figure 10:
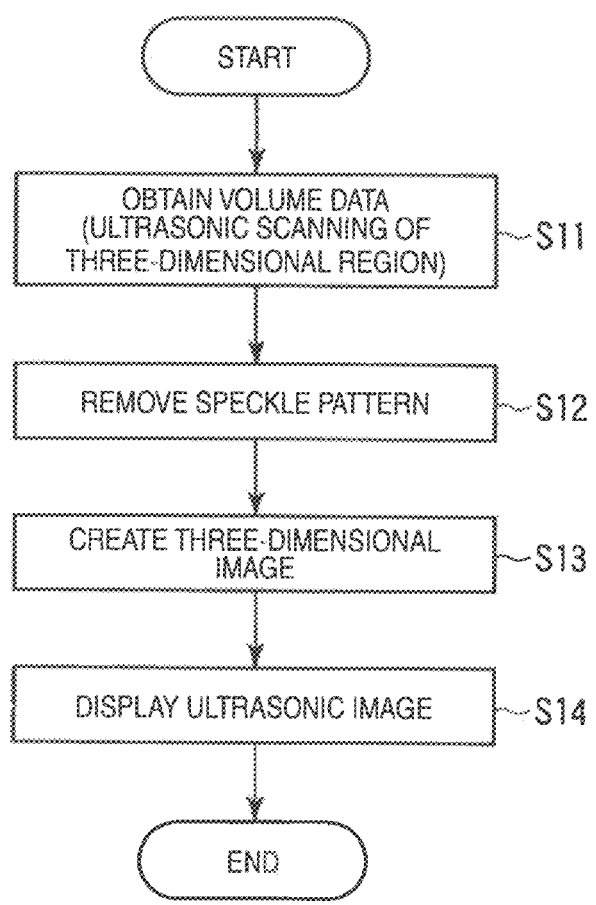
FIG. 10 is a flowchart showing a sequence of the speckle pattern removal process according to a third embodiment.

FIG. 10 is a flowchart showing a sequence of the speckle pattern removal process according to the second embodiment. Hereinafter, the contents of the processes in the respective Steps will be described.

Volume Data Acquisition: Step S11

First, the ultrasonic scanning is performed on the three-dimensional region including a predetermined portion of the patient, and the echo signals obtained from the three-dimensional region are obtained. The B-mode processing unit 23 creates plural two-dimensional image data (raw data) by using the obtained echo signals. In addition, the volume data creating unit 31 creates the volume data by using the created plural two-dimensional image data (Step S11).

Figure 11:
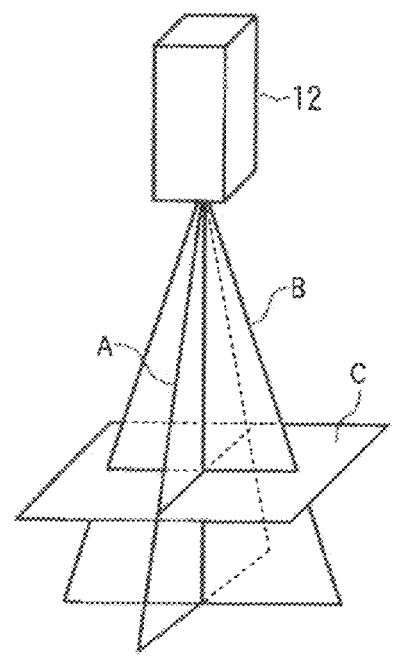
FIG. 11 is a diagram illustrating A, B, and C planes in an ultrasonic image diagnosis.
Figure 12:
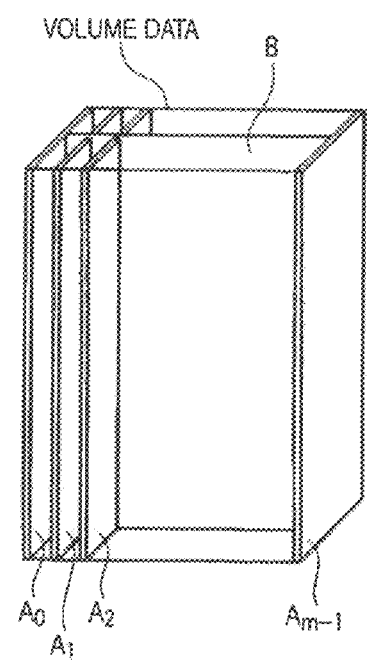
FIG. 12 is a diagram illustrating volume data created in Step S11.

FIG. 11 is a diagram illustrating A, B, and C planes in an ultrasonic image diagnosis. FIG. 12 is a diagram illustrating the volume data created in Step S11. As shown in FIG. 11, in the case of the ultrasonic probe 12 configured as the two-dimensional array probe, two planes intersecting the central axis of the ultrasonic probe 12 and intersecting each other in the perpendicular direction are respectively denoted by the A and B planes, and the plane perpendicular to the central axis and the A and B planes is denoted by the C plane. As shown in FIG. 12, the volume data in Step S11 includes image data (or interpolation data using the image data) of m number of two-dimensional images $A_0, A_1 \ldots A_{m-1}$ parallel to the A plane.

Speckle Pattern Removal Process: Step S12

Next, the speckle pattern removal processing unit 26 performs the speckle pattern removal process on the created volume data. That is, the speckle pattern removal processing unit 26 performs the speckle pattern removal process described in the first embodiment on the image data of the m number of two-dimensional images $A_0, A_1 \ldots A_{m-1}$ (Step S12).

Ultrasonic Image Creation and Display: Step S13 and Step S14

The image creating unit 25 performs processes such as a volume rendering, an MPR (multi planar reconstruction), and an MIP (maximum intensity projection) by using the volume data having been subjected to the speckle pattern removal process so as to create the three-dimensional image (Step S13). The created three-dimensional image is synthesized with the texts, the scales, or the like of various parameters by the image synthesizing unit 27, and the synthesized image is displayed as a predetermined form on the monitor 14 (Step S14).

According to the ultrasonic diagnostic apparatus, in the displayed three-dimensional image, the B and C planes are influenced by the advantage of the speckle pattern removal process as well as the A plane. Particularly, in the C plane required to be smooth, the speckle pattern is minute and the boundary surface of the tissue is clear. Accordingly, it is possible to realize the effective speckle pattern removal in the entire three-dimensional space.

Further, in the embodiment, the section subjected to the speckle pattern removal process is set to the A plane. However, the section corresponding to the target of the speckle pattern removal process is not limited to this example. That is, when the speckle pattern removal process is performed on the arbitrary section included in the volume data, it is possible to obtain the same advantage.

Third Embodiment

Next, a third embodiment of the invention will be described. In the second embodiment, an example is shown in which the speckle pattern removal process is performed on the volume data (i.e. the volume data including the raw data) before creating the three-dimensional image. On the contrary, in the embodiment, an example will be described in which the speckle pattern removal process is performed on the volume data (i.e. the volume data including the image data) after creating the three-dimensional image. In addition, the block diagram showing the configuration of the ultrasonic diagnostic apparatus 1 according to the third embodiment is substantially the same as that of FIG. 9.

Figure 13:
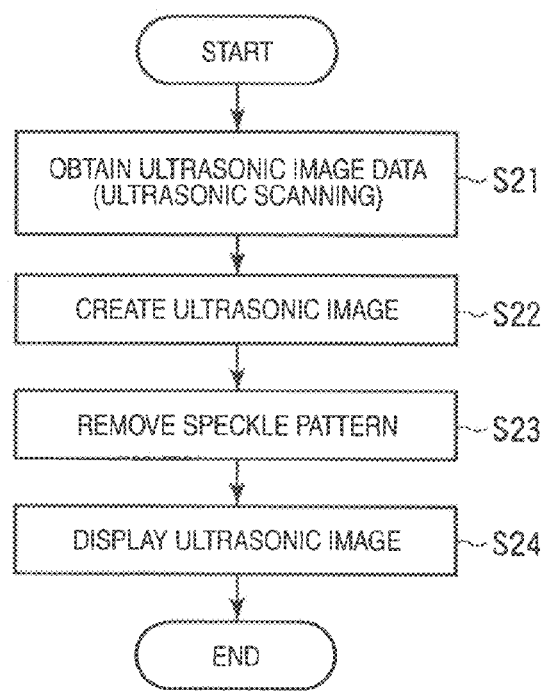
FIG. 13 is a flowchart showing a sequence of the speckle pattern removal process according to the third embodiment.

FIG. 13 is a flowchart showing a sequence of the speckle pattern removal process according to the third embodiment. Hereinafter, the contents of the processes of the respective Steps will be described.

Volume Data Acquisition: Step S21

First, in the same manner as the second embodiment, the ultrasonic scanning is performed on the three-dimensional region including a predetermined portion of the patient, and the echo signals obtained from the three-dimensional region are obtained. The B-mode processing unit 23 (or the Doppler processing unit 24) creates plural two-dimensional image data (raw data) by using the obtained echo signals. The volume data creating unit 31 creates the volume data by using the ultrasonic image data created by the B-mode processing unit 23 (Step S21).

Three-Dimensional Image Creation: Step S22

The image creating unit 25 performs processes such as volume rendering, MPR (multi planar reconstruction), MIP (maximum intensity projection), and surface rendering by using the created volume data so as to create one or more three-dimensional image (Step S22).

Speckle Pattern Removal Process: Step S23 Next, the speckle pattern removal processing unit 26 performs the speckle pattern removal process on one or more created three-dimensional image. The contents of the speckle pattern removal process have been already described above.

Ultrasonic Image Display: Step S24

The three-dimensional image having been subjected to the speckle pattern removal process is synthesized with the texts, the scales, or the like of various parameters by the image synthesizing unit 27, and the synthesized image is displayed as a predetermined form on the monitor 14 (Step S24).

Figure 14:
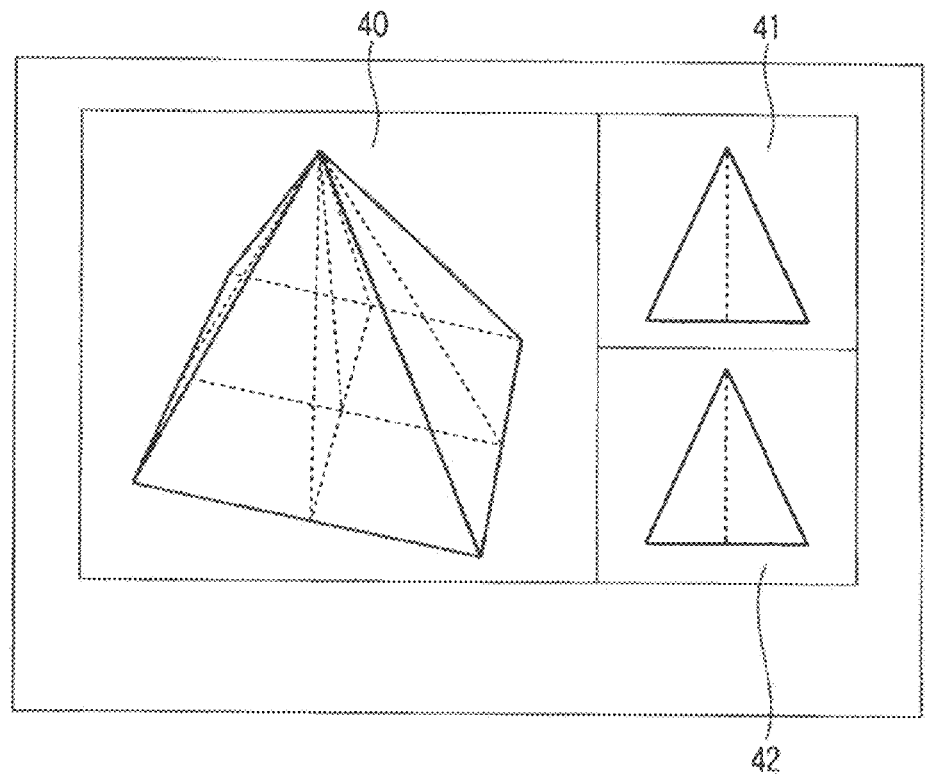
FIG. 14 is a diagram showing an example of a display pattern of a three-dimensional image having been subjected the speckle pattern removal process, where a volume rendering image and MPR images are displayed on a screen of a monitor.

FIG. 14 is a diagram showing an example of a display pattern of the three-dimensional image having been subjected the speckle pattern removal process, where the volume rendering image 40 and the MPR images 41 and 42 are displayed on the screen of the monitor 14. In the embodiment, the speckle pattern removal process is performed on at least one of the images, and the resultant image can be displayed. In addition, the common speckle pattern removal process parameter or the different speckle pattern removal process parameters may be performed on the respective images.

Even in the above-described ultrasonic diagnostic apparatus, it is possible to correct the unnatural image caused by the speckle pattern on the three-dimensional image by means of a comparatively small calculation amount.

Further, the invention is not limited to the above-described embodiments, but may be embodied by modifying the constituents without departing from the scope of the spirit of the invention. For example, the respective functions according to the embodiments may be realized in such a manner that the program for performing the respective processes is installed in a computer such as a workstation and the program is executed in a memory of the computer. At this time, the program capable of performing the respective methods according to the invention through the computer may be stored in a recording media such as a magnetic disc (a floppy (trademark) disc, a hard disc, or the like), an optical disc (a CD-ROM, a DVD, or the like), or a semiconductor memory, and may be distributed.

Furthermore, the plural constituents described in the above-described embodiments may be appropriately combined with each other to form various inventions. For example, several constituents may be omitted from all constituents shown in the above-described embodiments. The constituents of other embodiments may be appropriately combined with each other.

What is claimed is:

1. An ultrasonic diagnostic apparatus comprising:
a multi-resolution decomposition computer-implemented processor configured to perform a multi-resolution decomposition on ultrasonic image data so as to obtain first image data corresponding to a low-band signal component and at least one of second image data corresponding to a high-band signal component;
a reduction computer-implemented processor configured to perform a regional maximum value reduction process of reducing a regional maximum value lower than a first level and a regional minimum value reduction process of reducing a regional minimum value higher than a second level on the first image data and the at least one of the second image data; and
a reconstruction computer-implemented processor configured to perform a multi-resolution reconstruction by using the first image data and the at least one of the second image data having been subjected to the regional maximum value reduction process and the regional minimum value reduction process so as to create a reconstruction image;
wherein the reduction computer-implemented processor repeats the regional maximum value reduction process including a morphological dilation process and stops the regional maximum value when the first image data and the at least one of the second image data are converged, and determines when the first image data and the at least one of the second image data are converged for each image subject to the multi-resolution decomposition based on a comparison between a member image and a process image, and to change a number of times of executing the morphological dilation process for each image based on determining when the first image data and the at least one of the second image data are converged; and
the reconstruction computer-implemented processor performs the multi-resolution reconstruction by using the converged first image data and the converged at least one of the second image data.

2. The ultrasonic diagnostic apparatus according to claim 1,
wherein in the multi-resolution decomposition and the multi-resolution reconstruction, a Wavelet transform, a Wavelet inverse transform, or a Laplacian Pyramid method is used.

3. The ultrasonic diagnostic apparatus according to claim 1 or 2,
wherein the regional maximum value reduction process includes a morphological dilation process which is performed plural times.

4. The ultrasonic diagnostic apparatus according to claim 1,
wherein the regional maximum value reduction process includes a morphological erosion process which is performed plural times.

5. The ultrasonic diagnostic apparatus according to claim 1,
wherein the reduction computer-implemented processor is configured to invert the first image data and the at least one of the second image data after performing the region maximum value reduction process thereon, wherein the reduction computer-implemented processor is configured to perform the regional minimum value reduction process on the first inverted image data and the at least one of the second inverted image data, and wherein the reduction computer-implemented processor is configured to invert the first inverted image data and the at least one of the second inverted image data after performing the regional minimum value reduction process thereon.

6. The ultrasonic diagnostic apparatus according to claim 1, wherein the reduction computer-implemented processor is configured to invert the first image data and the at least one of the second image data after performing the region minimum value reduction process thereon, wherein the reduction computer-implemented processor is configured to perform the regional maximum value reduction process on the first inverted image data and the at least one of the second inverted image data, and wherein the reduction computer-implemented processor is configured to invert the first inverted image data and the at least one of the second inverted image data after performing the regional maximum value reduction process thereon.

7. The ultrasonic diagnostic apparatus according to claim 1, wherein the reduction computer-implemented processor is further configured to compare Ji with Ji+1 for each repetition in a repeated calculation loop, and, when Ji+1 is equal to Ji, regards repeated calculation as being converged and ends the loop.

8. The ultrasonic diagnostic apparatus according to claim 7, wherein the reduction computer-implemented processor is further configured to omit calculation of a minimum value extraction in pixels between a dilative marker and a mask for the already converged pixel.

9. The ultrasonic diagnostic apparatus according to claim 1, wherein the reduction computer-implemented processor is further configured to perform a speckle pattern removal process on a plurality of images, and the reconstruction unit creates volume data by synthesizing the plurality of processed images.

10. An ultrasonic image processing apparatus comprising:

an input configured to receive ultrasonic image data from an external device;

a multi-resolution decomposition computer-implemented processor configured to perform a multi-resolution decomposition on the ultrasonic image data so as to obtain first image data corresponding to a low-band signal component and at least one of second image data corresponding to a high-band signal component;

a reduction computer-implemented processor configured to perform a regional maximum value reduction process of reducing a regional maximum value lower than a first level and a regional minimum value reduction process of reducing a regional minimum value higher than a second level on the first image data and the at least one of the second image data; and a reconstruction computer-implemented processor configured to perform a multi resolution reconstruction by using the first image data and the at least one of the second image data having been subjected to the regional maximum value reduction process and the regional minimum value reduction process so as to create a reconstruction image, wherein the reduction computer-implemented processor repeats the regional maximum value reduction process including a morphological dilation process and stops the regional maximum value when the first image data and the at least one of the second image data are converged, and determines when the first image data and the at least one of the second image data are converged for each image subject to the multi-resolution decomposition based on a comparison between a member image and a process image, and to change a number of times of executing the morphological dilation process for each image based on determining when the first image data and the at least one of the second image data are converged; and the reconstruction computer-implemented processor performs the multi-resolution reconstruction by using the converged first image data and the converged at least one of the second image data.

11. The ultrasonic image processing apparatus according to claim 10, wherein in the multi-resolution decomposition and the multi-resolution reconstruction, a Wavelet transform, a Wavelet inverse transform, or a Laplacian Pyramid method is used.

12. The ultrasonic image processing apparatus according to claim 10, wherein the regional maximum value reduction process includes a morphological dilation process which is performed plural times.

13. The ultrasonic image processing apparatus according to claim 10, wherein the regional maximum value reduction process includes a morphological erosion process which is performed plural times.

14. The ultrasonic image processing apparatus according to claim 10, wherein the reduction computer-implemented processor is configured to invert the first image data and the at least one of the second image data after performing the region maximum value reduction process thereon, wherein the reduction computer-implemented processor is configured to perform the regional minimum value reduction process on the first inverted image data and the at least one of the second inverted image data, and wherein the reduction computer-implemented processor is configured to invert the first inverted image data and the at least one of the second inverted image data after performing the regional minimum value reduction process thereon.

15. The ultrasonic image processing apparatus according to claim 10, wherein the reduction computer-implemented processor is configured to invert the first image data and the at least one of the second image data after performing the region minimum value reduction process thereon, wherein the reduction computer-implemented processor is configured to perform the regional maximum value reduction process on the first inverted image data and the at least one of the second inverted image data, and wherein the reduction computer-implemented processor is configured to invert the first inverted image data and the at least one of the second inverted image data after performing the regional maximum value reduction process thereon.

16. The ultrasonic image processing apparatus according to claim 10,
wherein the reduction computer-implemented processor is further configured to compare Ji with Ji+1 for each repetition in a repeated calculation loop, and, when Ji+1 is equal to Ji, regards repeated calculation as being converged and ends the loop.

17. The ultrasonic image processing apparatus according to claim 16,
wherein the reduction computer-implemented processor is further configured to omit calculation of a minimum value extraction in pixels between a dilative marker and a mask for the already converged pixel.

18. The ultrasonic image processing apparatus according to claim 10,
wherein the reduction computer-implemented processor is further configured to perform a speckle pattern removal process on a plurality of images, and
the reconstruction computer-implemented processor creates volume data by synthesizing the plurality of processed images.

* * * * *